(12) United States Patent
Marrodan

(10) Patent No.: US 7,029,706 B2
(45) Date of Patent: Apr. 18, 2006

(54) COMPOSITION FOR THE TREATMENT OF CUTANEOUS MYCOSIS

(76) Inventor: Carlos Alberto Marrodan, Cordoba 58, Martinez, Buenos Aires (AR) 1640

( * ) Notice: Subject to any disclaimer, the term of this patent is extended or adjusted under 35 U.S.C. 154(b) by 68 days.

(21) Appl. No.: 10/301,136

(22) Filed: Nov. 21, 2002

(65) Prior Publication Data

US 2003/0072806 A1    Apr. 17, 2003

Related U.S. Application Data

(63) Continuation-in-part of application No. 09/970,178, filed on Oct. 4, 2001, now abandoned.

(51) Int. Cl.
| | |
|---|---|
| *A61K 9/14* | (2006.01) |
| *A61K 33/00* | (2006.01) |
| *A61K 33/18* | (2006.01) |
| *A61K 33/22* | (2006.01) |
| *A61K 31/085* | (2006.01) |
| *A61K 31/27* | (2006.01) |
| *A61K 31/4164* | (2006.01) |
| *A61K 31/47* | (2006.01) |
| *A61K 31/60* | (2006.01) |
| *A61P 17/00* | (2006.01) |
| *A61K 31/00* | (2006.01) |
| *A61K 31/28* | (2006.01) |

(52) U.S. Cl. .................. 424/724; 424/489; 424/490; 424/658; 424/659; 424/672; 424/771; 424/775; 514/25; 514/27; 514/159; 514/161; 514/162; 514/163; 514/164; 514/311; 514/396; 514/397; 514/398; 514/399; 514/400; 514/401; 514/402; 514/403; 514/450; 514/451; 514/456; 514/460; 514/479; 514/481; 514/560; 514/568; 514/717; 514/858; 514/865; 514/887; 514/951

(58) Field of Classification Search ............... 424/489, 424/490, 658–659, 724, 771, 775, 672; 514/25, 514/27, 159, 161–164, 311, 396–403, 450–451, 514/456, 460, 479, 481, 568, 717, 858, 865, 514/887, 951, 560

See application file for complete search history.

(56) References Cited

FOREIGN PATENT DOCUMENTS

JP        2-250833        * 10/1990

OTHER PUBLICATIONS

Derwent Abstract, accession No. 1990-345662, abstracting JP 2-250833 (1990).*
Chemical Abstracts 114:109017 (1991), abstracting JP 2-250833.*
Brantley, S. L. et al., "Surface area and porosity of primary silicate minerals," American Mineralogist, vol. 85, pp. 1767-1783 (2000).*
Kirk-Othmer Encyclopedia of Chemical Technology, John Wiley & Sons, NY, 4th ed., 1997, vol. 21, pp. 977-1002, 1020-1021, 1026-1027.*
Conversion US Mesh (tamis) -microns. Datasheet [online]. [retrieved on Aug. 15, 2005]. Retrieved from the Internet:, URL: www.granuloshop.com/Conversion.htm>.*
Sieve Size No. (US mesh). Datasheet [online]. elementsix. [retrieved on Aug. 15, 2005]. Retrieved from the Internet: <URL: www.e6.com/e6/page.jsp?pageid=600409510>.*

* cited by examiner

*Primary Examiner*—John Pak

(57) ABSTRACT

The inventions relates to the use of silica in the formulation of antifungal composition for the treatment of cutaneous mycoses, and method to manufacture an antifungal powder with boric acid and silica.

6 Claims, No Drawings

COMPOSITION FOR THE TREATMENT OF CUTANEOUS MYCOSIS

CROSS-REFERENCE TO RELATED APPLICATIONS

This application is a continuation-in-part of U.S. application Ser. No. 09/970,178, filed on Oct. 4, 2001, now abandoned.

BACKGROUND OF THE INVENTION

The present invention relates to the use of silica powder as dispersing agent and filler with antifungal drugs for the treatment of fungal infection of the skin. The present invention further relates to a method to manufacture an antifungal powder.

Most drugs currently available for the treatment of mycoses have limited efficacy, because they are used in low concentration owing to their high toxicity. Their beneficial effects, depends in the vehicle used.

Prior art formulations of fungicides used as carrier or diluent, liquid suspension, ointment, cataplasm, liniment, lotion Mycoses (e.g., athlete's foot) is a skin fungal infection that primarily occurs at moist parts of the body. So, when cream, gel or ointment preparations is applied to the affected part, it makes the affected part even more moist.

To avoid the skin moisture it is convenient that the preparation be in powder form. Prior art formulations in powder form used starch, talc, alum, borate as a vehicle.

U.S. Pat. No. 992,937 describes a nursery powder that combines boric acid with talcum powder as a vehicle U.S. Pat. No. 2,289,125 describes a combination of boric acid and tannic acid used in powder form with corn starch as filler for the treatment of fungus infection.

U.S. Pat. No. 4,816,254 describes another combination of boric acid and used in form of ointment, U.S. Pat. No. 4,935,241 describes a pharmaceutical preparation for tinea pedis with croconazole hydrochloride and a copolymer in an aqueous alcohol vehicle.

U.S. Pat. No. 5,711,954 describes an antifungal powder composition using imidazole compound in combination with talc coated with a hydrophobic coating.

In U.S. Pat. No. 5,994,403 a liquid solution of tannic acid is used for the treatment of fungal skin infections In U.S. Pat. No. 6,399,108 boric acid is used in combination with borate salt.

Starch may be avoided because it feeds any bacteria or fungi that may be present Talc or talcum powder is a hydrous magnesium silicate, with alkaline impurities, sticks to the skin, and keeps the skin moisturized. With certain imidazole compounds, show significant degradation of the active ingredient during storage.

Alum is a potassium or ammonium aluminum sulfate, and has alkaline molecules that favors fungus grow.

Borate salt, sodium tetraborate is alkaline.

SUMMARY OF THE INVENTION

The novelty of the present invention is the silica powder used as excipient Silica with acidic properties is by itself inhospitable for fungus. The acidic character of silica (silicon dioxide) is shown by its reaction with a large number of basic oxides to form silicates

DESCRIPTION OF THE INVENTION

Natural silica is obtained principally from quartz mineral because of its great purity. To obtain a nonabrasive powder, it must be ground at minus 325 mesh.

Crystalline silica obtained from high purity quartz is more than 99% $SiO_2$ and show great stability up to 870° C., it is chemically inert at ordinary temperature.

Fumed silica (aerosils) are produced by vapor-phase processes and particle size is lower than 1 micron.

Topical antifungal non-prescription drug products for over-the-counter human use authorized by the Food and Drug Administration are any one of the following within the specified concentration;

| | |
|---|---|
| (a) Clioquinol 3 percent | (e) Tolnafnate .1 percent |
| (b) Haloprogin 1 percent | (f) Undecylenic acid 10 to 25 percent |
| (c) Miconazole Nitrate 2 percent | (g) Clotrimazol 1 percent |
| (d) Povidone.iodine 10 percent | |

Mild antifungal are boric acid, tannic acid and the keratolytic agents such as salicylic acid and benzoic acid We can manufacture an antifungal powder composition using silica powder as dispersant of boric acid, with the property to relieve the irritation of the infected skin, used alone or in combination with tannic acid also antifungal, at the same time exert a toughening and healing action in the skin tissue.

Silica powder impede the agglomeration when the solution of boric acid is dispersed and dried because boric acid crystallize like waxy plates.

Determination of fungicidal power of 5% boric acid with different excipients:
a) Silica b) Sterilized talc c) Maize starch Microorganism Trychophyton Mentagrophytes

| agar diffusion test | inhibition zone (mm.) |
|---|---|
| a) Silica | 20 |
| b) Sterilized talc | 10 |
| c) Maize starch | 0 |

The test confirm that it is superior the inhibition obtained using silica as vehicle of the antifungal powder.

The process to manufacture an antifungal composition also includes:
a) Preparing a solution that contains between 0.1 to 5 wt. % boric acid and 0.1 to 5 wt. % tannic acid in a solvent selected from the group consisting of warm distilled water, warm demineralized water and alcohol.
b) Wetting an amount of silica powder (mesh 325) with the same weight amount of said solution to obtain a creamy consistency, and
c) drying and grinding the dried lumps to a powder to obtain the antifungal powder composition.

I claim:

1. An antifungal powder composition for the treatment of cutaneous mycosis that consists essentially of 70 to 99 weight percent natural quartz and at least one antifungal agent selected from the group consisting of organic antifungal agents and boric acid, and mixtures thereof.

2. An antifungal powder composition according to claim 1, wherein said antifungal agent is an azole derivative.

3. An antifungal powder composition according to claim 2, wherein the azole derivative is selected from the group consisting of miconazole, clotrimazole and econazole, and mixtures thereof.

4. An antifungal powder composition according to claim 1, wherein said antifungal agent is selected from the group consisting of undecylenic acid, haloprog in, clioquinol, tolnaftate and povidone-iodine, and mixtures thereof.

5. An antifungal powder composition according to claim 1, wherein said antifungal agent is selected from the group consisting of boric acid, tannic acid, salicylic acid and benzoic acid, and mixtures thereof.

6. A method of preparing an antifungal powder composition comprising the steps of:
   (a) Preparing a solution that contains between 0.1 to 5 wt. % boric acid and 0.1 to 5 wt. % tannic acid in a solvent selected from the group consisting of warm distilled water, warm demineralized water and alcohol;
   (b) Wetting an amount of silica powder (mesh 325) with the same weight amount of said solution to obtain a creamy consistency; and
   (c) Drying and grinding the dried lumps to a powder to obtain the antifungal powder composition.

* * * * *